United States Patent
Jin et al.

(10) Patent No.: US 10,857,575 B2
(45) Date of Patent: Dec. 8, 2020

(54) SHELF-LIFE-IMPROVED NANOSTRUCTURED IMPLANT SYSTEMS AND METHODS

(71) Applicant: Nanovation Partners LLC, Camarillo, CA (US)

(72) Inventors: Sungho Jin, San Diego, CA (US); Daniel F. Justin, Orlando, FL (US)

(73) Assignee: Nanovation Partners LLC, Camarillo, CA (US)

( * ) Notice: Subject to any disclaimer, the term of this patent is extended or adjusted under 35 U.S.C. 154(b) by 44 days.

(21) Appl. No.: 15/907,149

(22) Filed: Feb. 27, 2018

(65) Prior Publication Data
US 2018/0243803 A1    Aug. 30, 2018

Related U.S. Application Data

(60) Provisional application No. 62/464,268, filed on Feb. 27, 2017.

(51) Int. Cl.
*B08B 7/00* (2006.01)
*B08B 11/00* (2006.01)
(Continued)

(52) U.S. Cl.
CPC ............ *B08B 7/0057* (2013.01); *A61B 90/70* (2016.02); *A61L 2/14* (2013.01); *A61L 27/06* (2013.01);
(Continued)

(58) Field of Classification Search
CPC ..... B08B 7/0057; B08B 11/00; B08B 7/0071; B08B 17/065; A61B 90/70; A61L 2/08;
(Continued)

(56) References Cited

U.S. PATENT DOCUMENTS 6,250,984 B1    6/2001   Jin et al.
6,283,812 B1    9/2001   Jin et al.
(Continued)

FOREIGN PATENT DOCUMENTS

GB    2420712 A  *  6/2006  ............... A61L 2/14
JP    2002141633 A     5/2002
(Continued)

OTHER PUBLICATIONS

International Search Report and Written Opinion for corresponding International Application No. PCT/US2018/020035 dated Jun. 21, 2018.
(Continued)

*Primary Examiner* — Sharidan Carrillo
(74) *Attorney, Agent, or Firm* — David Meibos; Maywood IP Law

(57) ABSTRACT

Methods and treatments for removing contaminants from nanotube surfaces covering a medical device are disclosed herein. These methods and treatments include commencing exposure of a nanotube surface to at least one condition that at least partially removes the contaminants including: ultraviolet light, elevated temperature, plasma, and/or combinations thereof. These methods and treatments may also include orienting the nanotube surface relative to the at least one condition in order to enhance removal of the contaminants by the at least one condition. Exposure of the nanotube surface to the at least one condition may be ceased after the contaminants are at least partially removed from the nanotube surface.

21 Claims, 6 Drawing Sheets

(51) Int. Cl.
*B08B 3/04* (2006.01)
*A61L 2/14* (2006.01)
*A61L 31/08* (2006.01)
*A61L 31/16* (2006.01)
*A61B 90/70* (2016.01)
*A61L 27/06* (2006.01)
*A61L 27/50* (2006.01)
*A61L 2/10* (2006.01)
*B82Y 5/00* (2011.01)
*B82Y 40/00* (2011.01)
*B08B 17/06* (2006.01)

(52) U.S. Cl.
CPC ............ *A61L 27/50* (2013.01); *A61L 31/086* (2013.01); *A61L 31/088* (2013.01); *A61L 31/16* (2013.01); *B08B 3/041* (2013.01); *B08B 7/0071* (2013.01); *B08B 11/00* (2013.01); *A61L 2/10* (2013.01); *A61L 2202/24* (2013.01); *A61L 2300/406* (2013.01); *A61L 2300/412* (2013.01); *A61L 2400/12* (2013.01); *A61L 2400/18* (2013.01); *B08B 17/065* (2013.01); *B82Y 5/00* (2013.01); *B82Y 40/00* (2013.01)

(58) Field of Classification Search
CPC ... A61L 2/10; A61L 2/14; A61L 27/06; A61L 27/50; A61L 31/086; A61L 31/088; A61L 31/16; A61L 2202/24; A61L 2300/406; A61L 2300/412; A61L 2400/12; A61L 2400/18; B82Y 5/00; B82Y 40/00
See application file for complete search history.

(56) References Cited

U.S. PATENT DOCUMENTS

| | | |
|---|---|---|
| 6,286,226 B1 | 9/2001 | Jin |
| 6,297,063 B1 | 10/2001 | Brown et al. |
| 6,297,592 B1 | 10/2001 | Gore et al. |
| 6,322,713 B1 | 11/2001 | Choi et al. |
| 6,383,923 B1 | 5/2002 | Brown et al. |
| 6,465,132 B1 | 10/2002 | Jin |
| 6,504,292 B1 | 1/2003 | Choi et al. |
| 6,538,367 B1 | 3/2003 | Choi et al. |
| 6,741,019 B1 | 5/2004 | Filas et al. |
| 6,803,725 B2 | 10/2004 | Jin |
| 6,864,162 B2 | 3/2005 | Jin |
| 6,900,421 B2* | 5/2005 | Varma .................. A61C 19/002 219/679 |
| 6,987,027 B2 | 1/2006 | Jin |
| 7,012,266 B2 | 3/2006 | Jin |
| 7,465,210 B2 | 12/2008 | Kim et al. |
| 7,576,341 B2 | 8/2009 | Kim et al. |
| 7,735,147 B2 | 6/2010 | Jin et al. |
| 7,820,064 B2 | 10/2010 | Jin |
| 7,959,830 B2 | 6/2011 | Jin |
| 8,020,216 B2 | 9/2011 | Jin |
| 8,178,165 B2 | 5/2012 | Jin |
| 8,182,783 B2* | 5/2012 | Mitra .................... B82Y 30/00 423/461 |
| 8,333,948 B2 | 12/2012 | Pak et al. |
| 8,414,908 B2 | 4/2013 | Jin et al. |
| 8,478,378 B2 | 7/2013 | Lal et al. |
| 9,108,880 B2 | 8/2015 | Jin et al. |
| 9,365,427 B2* | 6/2016 | Lee ........................ C01B 32/17 |
| 9,368,289 B2 | 6/2016 | Jin et al. |
| 9,555,159 B2 | 1/2017 | Jin et al. |
| 9,623,151 B2 | 4/2017 | Jin et al. |
| 9,867,903 B2 | 1/2018 | Jin et al. |
| 9,907,876 B2 | 3/2018 | Jin et al. |
| 9,956,743 B2 | 5/2018 | Jin et al. |
| 2001/0008157 A1 | 7/2001 | Bishop et al. |
| 2002/0114949 A1 | 8/2002 | Bower et al. |
| 2002/0159917 A1 | 10/2002 | Swart et al. |
| 2002/0198601 A1 | 12/2002 | Bales et al. |
| 2003/0093107 A1* | 5/2003 | Parsonage .............. A61F 2/01 606/194 |
| 2003/0133637 A1 | 7/2003 | Bao et al. |
| 2004/0036407 A1 | 2/2004 | Jin |
| 2004/0062177 A1 | 4/2004 | Jin |
| 2004/0071951 A1 | 4/2004 | Jin |
| 2004/0127012 A1 | 7/2004 | Jin |
| 2004/0150311 A1 | 8/2004 | Jin |
| 2004/0232358 A1* | 11/2004 | Moruzzi .................. A23L 3/28 250/504 R |
| 2005/0079282 A1 | 4/2005 | Jin |
| 2005/0158221 A1* | 7/2005 | McNulty ................ A61L 2/202 422/186.07 |
| 2005/0238810 A1* | 10/2005 | Scaringe .............. B82Y 30/00 427/249.1 |
| 2005/0252805 A1 | 11/2005 | Cervantes |
| 2006/0057388 A1 | 3/2006 | Jin et al. |
| 2006/0249391 A1 | 11/2006 | Jin |
| 2007/0207318 A1 | 9/2007 | Jin et al. |
| 2007/0235772 A1 | 10/2007 | Jin et al. |
| 2007/0238184 A1 | 10/2007 | Lal et al. |
| 2008/0054790 A1 | 3/2008 | Kim et al. |
| 2008/0098805 A1 | 5/2008 | Jin et al. |
| 2009/0098671 A1 | 4/2009 | Kim et al. |
| 2009/0192429 A1* | 7/2009 | Daniels ................ D06M 23/08 602/43 |
| 2009/0220561 A1* | 9/2009 | Jin ....................... A61K 9/0009 424/423 |
| 2009/0250588 A1 | 10/2009 | Robeson et al. |
| 2010/0005553 A1 | 1/2010 | Jin et al. |
| 2010/0229265 A1 | 9/2010 | Jin et al. |
| 2011/0116967 A1 | 5/2011 | Roy et al. |
| 2012/0032566 A1* | 2/2012 | Liu ...................... B29C 37/0053 312/223.1 |
| 2012/0288699 A1 | 11/2012 | Ahlberg et al. |
| 2013/0022494 A1* | 1/2013 | Kirkpatrick ............ H01J 37/08 422/22 |
| 2013/0189156 A1* | 7/2013 | Keener .................... A61L 2/20 422/29 |
| 2013/0323119 A1 | 12/2013 | Alwan |
| 2014/0086962 A1 | 3/2014 | Jin et al. |
| 2014/0256078 A1 | 9/2014 | Jin et al. |
| 2016/0067388 A1* | 3/2016 | Kipper .................... A61L 31/10 424/423 |
| 2016/0071655 A1 | 3/2016 | Li et al. |
| 2016/0088853 A1* | 3/2016 | Tikekar .................. A23L 3/28 426/305 |
| 2016/0261005 A1 | 9/2016 | Rtomji et al. |
| 2017/0007743 A1 | 1/2017 | Hedrick et al. |
| 2017/0138646 A1 | 5/2017 | Ihnfeldt et al. |
| 2017/0216494 A1* | 8/2017 | Roth ..................... A61L 31/022 |
| 2017/0243803 A1* | 8/2017 | Lin ........................ H01L 23/13 |
| 2017/0360974 A1* | 12/2017 | Fregoso ................. A61L 2/14 |
| 2018/0066875 A1 | 3/2018 | Ihnfeldt et al. |
| 2018/0243803 A1 | 8/2018 | Jin et al. |
| 2018/0272048 A1* | 9/2018 | Gifford ................. A61L 27/06 |
| 2018/0297839 A1 | 10/2018 | Jin et al. |
| 2018/0361704 A1 | 12/2018 | Jin et al. |
| 2019/0041378 A1 | 2/2019 | Choi et al. |
| 2019/0117827 A1* | 4/2019 | Roth ..................... A61L 27/06 |

FOREIGN PATENT DOCUMENTS

| | | |
|---|---|---|
| WO | 2006043166 A2 | 4/2006 |
| WO | WO2018098286 A1 | 5/2018 |

OTHER PUBLICATIONS

Mandracci et al. "Surface Treatments and Functional Coatings for Biocompatibility Improvement and Bacterial Adhesion Reduction in Dental Implantology", Coatings 2016, 6(7):8-15 and 2-22.

Pankova et al. "Investigation of the effect of HF-plasma on the chemical composition of collagen and keratin-containing HMM on the example of model compounds", Doctor of Engineering Science 2012, pp. 81-83 (Google machine translation).

(56) References Cited

OTHER PUBLICATIONS

Hajime Minamikawa, Wael Att, Takayuki Ikeda, Makoto Hirota and Takahiro Ogawa. Long-Term Progressive Degradation of the Biological Capacity of Titanium. 2016. www.mdpi.com/journal/materials.

Wael Att, Norio Hori, Masato Takeuchi, Jianyong Ouyang, Yang Yang, Masakazu Anpo and Takahiro Ogawa. Time-dependent degradation of titanium osteoconductivity: An implication of biological aging of implant materials. Jul. 11, 2009. www.elsevier.com/locate/biomaterials.

Hideki Aita, Norio Hori, Masato Takeuchi, Masahiro Yamada, Masakazu Anpo and Takahiro Ogawa. The effect of ultraviolet functionalization of titanium on integration with bone. Nov. 29, 2008. www.elsevier.com/locate/biomaterials.

Yang, et al., "Effect of annealing temperature on wettability of TiO2 nanotube array films", Nanoscale Research Letters (2014), 9:621 (7 pp.).

* cited by examiner ial Patent Application Ser. No. 62/464,268, entitled SHELF-LIFE-IMPROVED NANOSTRUCTURED IMPLANT SYSTEMS AND METHODS

SHELF-LIFE-IMPROVED NANOSTRUCTURED IMPLANT SYSTEMS AND METHODS

CROSS-REFERENCE TO RELATED APPLICATIONS

The present application claims the benefit of U.S. Provisional Patent Application Ser. No. 62/464,268, entitled SHELF-LIFE-IMPROVED BONE AND DENTAL IMPLANTS COMPRISING TITANIUM OXIDE OR ZIRCONIUM OXIDE NANOTUBES, METHODS AND USES THEREOF, which was filed on Feb. 27, 2017. The above application is incorporated by reference herein as though set forth in its entirety.

TECHNICAL FIELD

The present disclosure relates to medical devices such as orthopedic implants, dental implants, in vitro biomedical implants, in vivo biomedical implants, cell growth devices, drug delivery devices, etc., all of which may benefit from an improved shelf life.

BACKGROUND

It is well known that nano-scaled materials exhibit extraordinary electrical, optical, magnetic, chemical, and/or biological properties all of which may not be achieved via micro-scaled or bulk counterparts. In recent years, the development of nano-scaled materials has been intensively pursued in order to utilize such properties for various technical applications including biomedical and nano-bio applications. For example, nanoscale titanium oxide structures are set forth in: U.S. patent application Ser. No. 11/913,062, filed Jun. 10, 2008 and entitled "COMPOSITIONS COMPRISING NANOSTRUCTURES FOR CELL, TISSUE AND ARTIFICIAL ORGAN GROWTH, AND METHODS FOR MAKING AND USING SAME," now U.S. Pat. No. 8,414,908; U.S. patent application Ser. No. 13/858,042, filed Apr. 6, 2013 and entitled COMPOSITIONS COMPRISING NANOSTRUCTURES FOR CELL, TISSUE AND ARTIFICIAL ORGAN GROWTH, AND METHODS FOR MAKING AND USING SAME, now U.S. Pat. No. 927,327; and U.S. patent application Ser. No. 15/043,382, filed Feb. 12, 2016 and entitled COMPOSITIONS COMPRISING NANOSTRUCTURES FOR CELL, TISSUE AND ARTIFICIAL ORGAN GROWTH, AND METHODS FOR MAKING AND USING SAME, all of which are incorporated by reference herein as though set forth in their entirety.

Titanium (Ti) metal and Ti alloys such as Titanium-Aluminum-Vanadium (Ti—Al—V) are corrosion resistant, machinable, and light, yet sufficiently strong for load-bearing applications. They are one of the few biocompatible metals which osseo-integrate with bone material (e.g., by allowing direct chemical and/or physical bonding with adjacent bone surfaces without forming a fibrous tissue interface layer). For these reasons, Ti and Ti alloys have been used successfully in orthopedic and dental implants. See Handbook of biomaterial properties, edited by J. Black and G. Hasting, London; Chapman & Hall, 1998, and Biomaterials Science, a book by B. D. Ratner et al., San Diego, Calif.: Academic press; 1996.

The bioactivity of Ti, such as the relatively easy formation of hydroxyapatite type bone mineral on Ti, is primarily caused by the occurrence of Titanium Oxide ($TiO_2$) on the surface of Ti and its alloys. Among the various crystal structures of $TiO_2$, the anatase phase is known to be better than the rutile phase of $TiO_2$ (and other phases). See an article by Uchida et al, Journal of Biomedical Materials Research, Vol. 64, page 164-170 (2003).

Surface treatments such as roughening by sand blasting, formation of anatase phase $TiO_2$, hydroxyapatite coating, or other chemical treatments, have been utilized to further improve the bioactivity of the Ti surface and enhance bone growth. Accelerated bone growth may be accomplished when the surface of Ti, or a Ti-6Al-4V alloy type implant, is anodized to form amorphous $TiO_2$ nanotubes. The $TiO_2$ nanotube surface may then subsequently be annealed at 500° C. to 550° C. to crystallize the amorphous $TiO_2$ nanotubes and form more desirable anatase type $TiO_2$ nanotubes. The $TiO_2$ phase can be prepared by various techniques such as the sol-gel method, electrophoretic deposition, and anodization. See articles by. B. B. Lakshmi, et al., Chemistry of Materials, Vol. 9, page 2544-2550 (1997), Miao, et al., Nano Letters, Vol. 2, No. 7, page 717-720 (2002), Gong, et al., Journal of Materials Research, Vol 16, No 12, page 3331-3334 (2001), and J. M. Macak, et al., Angew. Chem. Int. Ed., Vol. 44, page 7463-7465 (2005).

An investigation of such anodized $TiO_2$ nanotubes for successful bone growth or other bio application has been reported. See an article by S. Oh et al, "Growth of Nanoscale Hydroxyapatite Using Chemically Treated Titanium Oxide Nanotubes", Biomaterials, vol. 26, page 4938-4943 (2005). Patients who go through Ti implant operations for repair of hip joints, broken bones, or dental implants often have to wait for many months of slow bone growth recovery before they are free of the need for bed rest or crutches and are able to return to a normal life. Accelerated bone growth would help the implants bond more rapidly and securely to bone, thus reducing the healing time for such patients.

Moreover, anodized $TiO_2$ nanotube arrays may exhibit highly hydrophilic properties which can be beneficial for good wetting properties and enhanced bone growth. Inadvertent accumulation of organic materials tends to reduce the hydrophilicity of anodized $TiO_2$ nanotube arrays, which causes a shelf-life problem as the degree of such organic, or carbonaceous film, generally increases with time. See articles by Att et al, "Time-dependent degradation of titanium osteoconductivity: An implication of biological aging of implant materials", Biomaterials 30, 5352-5363 (2009), by Hideki Aita et al, "The effect of ultraviolet functionalization of titanium on integration with bone", Biomaterials 30 (2009) 1015-1025, by Minamikawa et al, "Long-Term Progressive Degradation of the Biological Capability of Titanium", Materials 9, 102 (2016), by Hamlekhan, et al, "Fabrication of Anti-Aging $TiO_2$ Nanotubes on Biomedical Ti Alloys", PLOS ONE, 9(5), e96213 (May 2014, www-.plosone.org), and by Choi et al, "Time-dependent effects of ultraviolet and non-thermal atmospheric pressure plasma on the biological activity of titanium", Scientific Reports 6:33421, DOI: 10.1038/srep33421.

All of the above articles and references are incorporated by reference herein as though set forth in their entirety.

SUMMARY

In order to help reduce and/or remove the accumulation of organic materials on nanotube arrays, in particular on bone in-growth nanotube surfaces of implants, such nanotube surfaces may be treated with ultraviolet (UV) radiation. UV sterilization may be applied to the nanotube structures of implants or substrate materials having a variety of geometry and configurations. According to certain embodiments, sterilized and/or reactivated hydrophilic nanotube surface configurations may include TiO2 nanotubes as well as oxide nanotube surfaces formed from alloys containing Ti or TiO2 by at least 50% weight. However, the use of other related materials such as Zr, Hf, Nb, Ta, Mo, W, and their oxides, or alloys of these metals and oxides by at least 50% weight is also contemplated. Other materials such as Si, Si oxide, carbon, diamond, noble metals (such as Au, Ag, Pt and their alloys), polymer or plastic materials, or composite metals, ceramics or polymers can also be utilized to produce and use desired surface configurations for implant and cell growth applications.

In some embodiments, it may be advantageous for such implants to include a coating of Ti, TiO2, Zr, Hf, Nb, Ta, Mo, W and/or their oxides, and/or alloys thereof, with a thickness of at least 30 nm. In some embodiments, the coating may advantageously cover at least 70% of the total surface of the implant.

In some embodiments, one or more plasma-based methods may be used to reactivate Ti-based nanotube structures and related implants by decomposing the organic or carbon type surface contaminants, such as hydrocarbon based and/or carbon-containing contaminants, at a much faster rate than would be obtained through the use of UV light. Oxygen-based plasma, Argon-based plasma, Nitrogen-based plasma and/or other types of plasmas, and/or combinations/mixtures thereof may also be used, for example. Such plasma treatment may enable relatively rapid reactivation of the bone in-growth properties of the nanotube coating.

Additionally or alternatively, heat-based methods may be used to remove organic film layers. An implant with a nanotube coating as set forth above may be heated, for example, to a temperature of 400° C. or less to reactivate the bone in-growth properties of the surface.

In some embodiments, a method for removing contaminants from a medical device, that has a nanostructured surface may include commencing exposure of the nanostructured surface to at least one condition that at least partially removes the contaminants. The at least one condition may be selected from: ultraviolet light, an elevated temperature, and/or a plasma. The method may also include ceasing exposure of the nanostructured surface to the at least one condition after the contaminants are at least partially removed from the nanostructured surface. In these and other embodiments, the at least one condition may be applied to the nanostructured surface while it is in: a dry state, a wet state, and/or a protected state. Additionally, the method may also include orienting the nanostructured surface relative to the at least one condition to enhance removal of the contaminants by the at least one condition.

In other embodiments, a method for removing contaminants from a medical device, that has a nanotube surface having a plurality of nanotubes with inner nanotube surfaces and outer nanotube surfaces, may include commencing exposure of the nanotube surface to at least one condition that at least partially removes the contaminants. The at least one condition may be selected from: ultraviolet light, an elevated temperature, and/or a plasma. The method may also include ceasing exposure of the nanotube surface to the at least one condition after the contaminants are at least partially removed from the nanotube surface, including the inner nanotube surfaces and the outer nanotube surfaces. In these and other embodiments, the nanotube surface may include an oxide nanotube coating formed from alloys containing at least one of Ti or TiO2 by at least 50% weight. In a particular embodiment, the oxide nanotube coating may include TiO2 anatase crystals. In some embodiments, the oxide nanotube coating may have a thickness of at least 30 nm. In additional embodiments, the nanotube surface, and/or oxide nanotube coating, may cover at least 70% of a total surface of the medical device.

In further embodiments, a method for removing contaminants from a medical device, may include providing a medical device that has a substrate and a nanotube surface covering at least a portion of a surface of the substrate. The nanotube surface may include a plurality of nanotubes and the plurality of nanotubes may have a plurality of inner nanotube surfaces, a plurality of outer nanotube surfaces, and an oxide nanotube coating formed over the plurality of inner nanotube surfaces and outer nanotube surfaces. The method may also include commencing exposure of the nanotube surface to at least one condition that at least partially removes the contaminants. The at least one condition may be selected from: ultraviolet light, an elevated temperature, and/or a plasma. The method may also include ceasing exposure of the nanotube surface to the at least one condition after the contaminants are at least partially removed from the nanotube surface, including the inner nanotube surfaces and the outer nanotube surfaces. In these and other embodiments, the oxide nanotube coating may be formed from alloys containing at least one of Ti or TiO2 by at least 50% weight. In a particular embodiment, the oxide nanotube coating may include TiO2 anatase crystals. In some embodiments, the oxide nanotube coating may have a thickness of at least 30 nm. In additional embodiments, the nanotube surface, and/or oxide nanotube coating, may cover at least 70% of a total surface of the medical device.

In additional embodiments, a medical device may include surface nanotubes made from oxides having at least one of: Ti, Zr, V, Ta, Nb, Hf, Mo, and/or W. The surface nanotubes of the medical device may exhibit an increase in hydrophilicity after exposure to at least one condition that at least partially removes contaminants from the surface nanotubes of the medical device. The at least one condition may be selected from: ultraviolet light, an elevated temperature, and/or a plasma. Furthermore, the surface nanotubes of the medical device may substantially maintain their increased super-hydrophilic properties after undergoing a storage period of at least three months within a protected environment.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

Figures 1A, 1B:
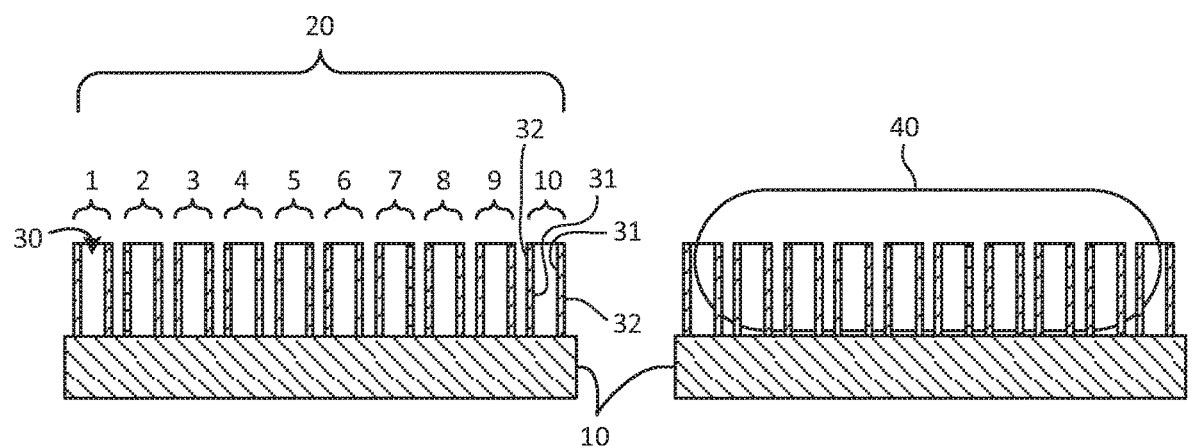
FIG. 1A illustrates a cross-sectional side view of a medical device that incorporates a nanotube surface.
FIGS. 1B-D illustrate how a water droplet may interact with the nanotube surface of FIG. 1A according to the presence (or absence) of organic contaminants on the nanotube surface.

It is to be understood that the drawings are for purposes of illustrating the concepts of the disclosure and are not to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the disclosure, as claimed, but is merely representative of exemplary embodiments of the disclosure.

Ti based implants may be prone to surface contamination when they come into contact with ambient air, water, cleaning solutions, other materials, and/or during storage of the implants. Implants with a $TiO_2$ nanotube surface may be different from regular Ti implants in that the $TiO_2$ coated nanotube surface includes vertically aligned, small-diameter (e.g., 30 to 300 nm diameter) and relatively tall (e.g., 100-2,000 nm height), tube-like nanostructures. $TiO_2$ nanotube surfaces may be particularly susceptible to surface contamination due to the higher reactivity of their nanoscale surfaces. Possible contaminants that may interact with the nanoscale surface may include, but are not limited to: oily matter, organic material, hydrocarbon based material, nitrogen-based material, sulfide-based material, and the like. These contaminants may slowly accumulate on the nanotube surface over an extended period of time (e.g., seconds, minutes, hours, days, months, years, etc.). A shelf-aged Ti or $TiO_2$ nanotube surface may lose its original super-hydrophilic characteristic, which is an important characteristic for the adhesion and growth of osteoblast cells, protein molecules, hydroxyapatite components, and the like. Moreover, longer exposure times typically result in more extensive contamination of the nanotube surface, resulting in a more severe loss of hydrophilicity. Accordingly, the shelf life characteristics of implantable materials is an important issue that must be addressed.

According to embodiments of the present disclosure, any of three approaches may be used to re-activate a $TiO_2$ coated nanotube surface (and/or other refractive metal oxide nanotubes as well), by decomposing and/or removing the oily matter, organic material, and/or hydrocarbon-based contaminants from the nanotube surface. These three approaches may include, but are not limited to: (1) UV exposure of the $TiO_2$ nanotube surface; (2) Re-activation thermal annealing at low temperature without introducing thermal stress and/or micro-cracking; and (3) More rapid re-activation of $TiO_2$ nanotube surface by using plasma bathing including, but not limited to: oxygen plasma, argon plasma, nitrogen plasma, and/or other suitable plasmas.

High-aspect ratio nanotubes may be difficult to clean and re-activate because the size and shape of high-aspect ratio nanotubes may naturally interfere with the above cleaning/re-activation processes. For example, the size and shape of high-aspect ratio nanotubes may make it more difficult to shine UV light into the interior of the nanotubes to sufficiently clean/reactivate the interior and/or exterior surfaces of the nanotubes. Accordingly, the present disclosure describes improved reactivation methods which may be particularly useful for implants that incorporate high-aspect-ratio nanotube structures.

FIG. 1A illustrates a cross-sectional side view of a medical device 10, or substrate 10, incorporating a nanostructured surface (or nanotube surface) 20 covering at least a partial surface of the medical device/substrate 10. The nanostructured surface 20 may be made predominantly of a plurality of nanotubes (1-10). In the example nanotube surface 20 depicted in FIG. 1A, ten nanotubes (1-10) are shown for the purposes of illustrating the general concepts disclosed herein. However, it will be understood that any number nanotubes are contemplated without departing from the spirit or scope of the present disclosure. In FIG. 1A, the ten nanotubes (1-10) shown each have inner bores 30 that define a plurality of inner nanotube surfaces 31 lying within the interior regions of the inner bores 30, as well as a plurality of outer nanotube surfaces 32 outside of the inner bores 30 of the nanotubes (1-10). Moreover, in at least some embodiments, the nanostructured surface 20 may also include micro-scale surface features and/or imperfections (not shown). In still further embodiments, the nanostructured surface 20 may further include at least one characteristic selected from: randomly structured nanopores, randomly structured nanorods, periodic structured nanopores, and/or periodic structured nanorods.

In some embodiments, the nanotube surface 20 may be anodized with a coating of $TiO_2$ nanotubes (1-10), which may then undergo an additional annealing process, and/or be packaged and stored according to techniques known in the art. In additional embodiments, the $TiO_2$ coated nanotube surface 20 may incorporate high-aspect-ratio nanotube structures (1-10) that: (1) may be substantially vertically aligned; (2) may have small-diameters (e.g., 30 nm to 300 nm); (3) may be relatively tall (e.g., 100 nm-2,000 nm in height; In some embodiments, the high-aspect-ratio nanotube structures (1-10) may have nanotube heights of less than 10 um); and/or (4) may have nanotube lateral dimensions less than 1,000 nm (In some embodiments, the high-aspect-ratio nanotube structures (1-10) may have nanotube lateral dimensions of less than 400 nm). In further embodiments, the nanotube surface 20 may include an oxide nanotube coating formed from alloys containing at least one of Ti or $TiO_2$ by at least 50% weight. In additional embodiments, the nanotube surface 20 may include an oxide nanotube coating formed from alloys containing at least one of Zr, V, Ta, Nb, Hf, Mo, W, or their oxides, by at least 50% weight. In yet further embodiments, the oxide nanotube coating may include $TiO_2$ anatase crystals. In yet additional embodiments, the oxide nanotube coating may have a thickness of at least 30 nm. In still further embodiments, the oxide nanotube coating may cover at least 70% of a total surface of the medical device.

In additional embodiments, the nanostructured surface 20 may also include at least one coating selected from: (1) a coating that includes hydroxyapatite with a thickness of at least 2 nm; (2) a coating that includes calcium; (3) a coating that includes potassium; (4) a coating that includes Ta; (5) a coating that includes Ta-oxide; (6) a coating that includes at least one biological agent and the coating is at least partially present on the plurality of inner nanotube surfaces 31; (7) a coating that includes at least one catalyst and the coating is at least partially present on the plurality of inner nanotube surfaces 31; (8) a coating that includes at least one catalyst and the coating is at least partially present on the plurality of inner nanotube surfaces 31; (9) a coating that includes at least one cell-growth-stimulating agent and the coating is at least partially present on the plurality of inner nanotube surfaces 31; (10) a coating that includes at least one antibiotic and the coating is at least partially present on the plurality of inner nanotube surfaces 31; and/or (11) any combination(s) of coatings thereof.

Figures 1C, 1D:
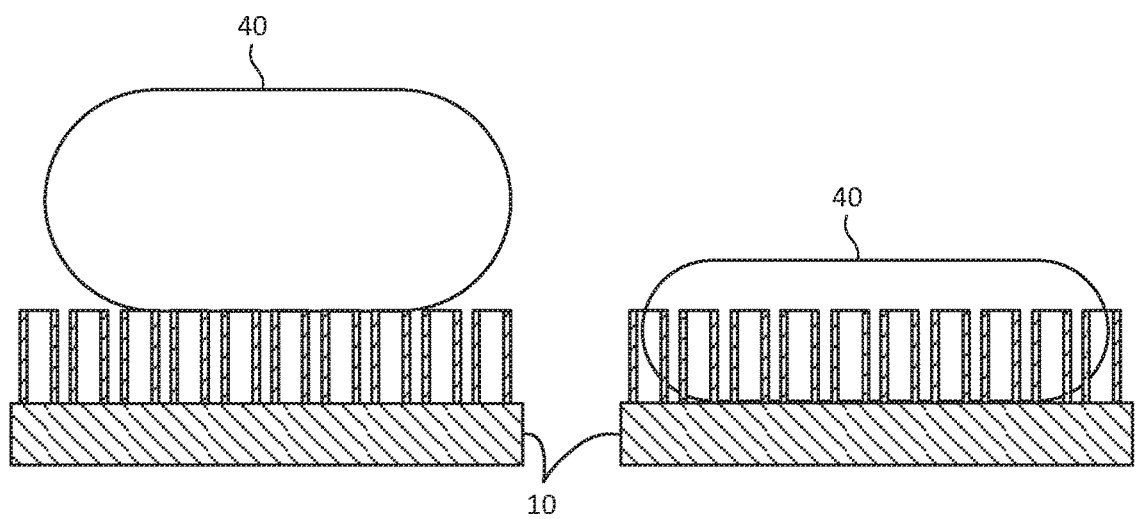

FIGS. 1B-D illustrate how a water droplet 40 may interact with the nanotube surface 20 of the medical device 10 of FIG. 1A according to the presence, or absence, of organic contaminants on the nanotube surface 20. More specifically, FIGS. 1B-D illustrate the hydrophobic/hydrophilic properties of the nanotube surface 20 and how a contact angle θ associated with the water droplet 40 placed on top of the nanotube surface 20 may vary due to the presence, or absence, of organic contaminants on the nanotube surface 20, thus affecting the hydrophobic/hydrophilic characteristics of the nanotube surface 20.

FIG. 1B depicts virgin/clean nanotubes on the surface of the medical device 10 of FIG. 1A. Since there are no (or at least very little) organic matter contaminants present on the nanotube surface 20 of the medical device 10 in FIG. 1B, the nanotube surface 20 retains its super-hydrophilic characteristics and readily absorbs the water droplet 40 into the nanotube structures, as is shown in FIG. 1B. The water droplet 40 shown in FIG. 1B may have a contact angle θ of about 0 to 10 degrees.

FIG. 1C depicts the medical device 10 of FIG. 1B after the nanotubes have become contaminated with organic matter. Since organic matter contaminants are present on the nanotube surface 20 of the medical device 10 in FIG. 1C, the nanotube surface 20 adopts a more hydrophobic characteristic which tends to repel the water droplet 40, preventing absorption of the water droplet 40 into the nanotube structures, as is shown in FIG. 1C. The water droplet 40 shown in FIG. 1B may have a contact angle θ of about 10 to 100 degrees.

FIG. 1D depicts the medical device 10 of FIG. 1C after the nanotubes have been processed by cleaning techniques disclosed herein to remove, or at least partially remove, the organic matter contaminants and restore the hydrophilic characteristics of the nanotubes, such that the nanotube surface 20 may once again readily absorb the water droplet 40 into the nanotube structures. The water droplet 40 shown in FIG. 1B may once again have a contact angle θ of about 0 to 10 degrees.

In summary, FIGS. 1B-D illustrate how the desired hydrophilicity of the nanotube surface 20 may be lost over time due to the time-dependent accumulation of organic, oily, hydrocarbon based, and/or carbon-containing contaminants through exposure to the air environment, or other materials, and how this hydrophilicity may then be recovered by cleaning processes described herein.

In general, the cleaning processes described herein may include commencing exposure of the nanotube surface 20, including the inner nanotube surfaces 31 and the outer nanotube surfaces 32, to at least one condition that at least partially removes the contaminants from the nanotube surface 20. The at least one condition may generally be selected from: ultraviolet light, an elevated temperature, and plasma. Once the at least one condition has at least partially removed from the contaminants from the nanotube surface 20, including the inner nanotube surfaces 31 and the outer nanotube surfaces 32, exposure of the nanotube surface 20 to the at least one condition may be ceased. These cleaning processes and conditions will be explained below in more detail.

Figures 2A, 2B:
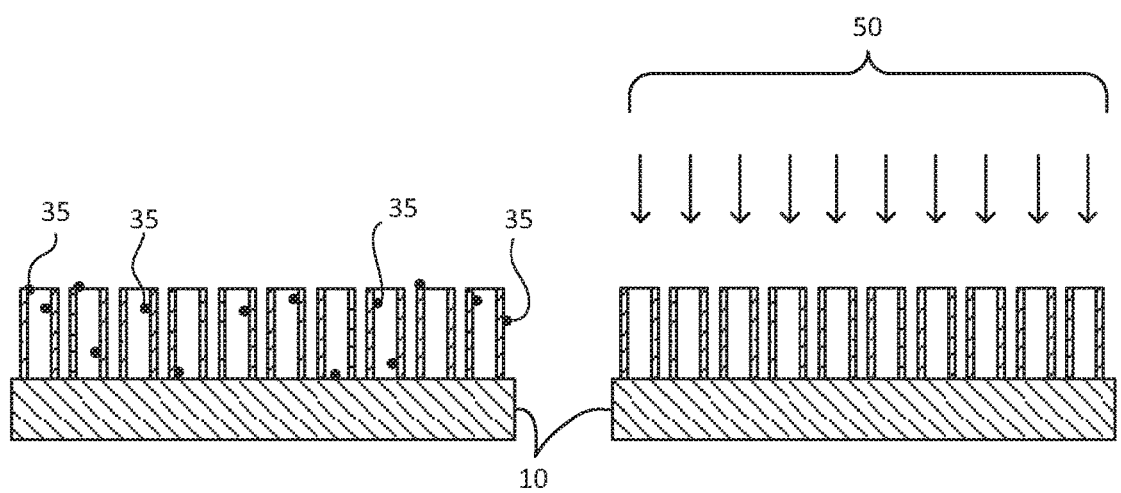
FIG. 2A illustrates the nanotube surface of FIG. 1A with organic matter contaminants on the nanotube surface.
FIGS. 2B-2D depict various ways of treating the nanotube surface of FIG. 1A with UV radiation to remove the organic matter contaminants.
Figures 2C, 2D:
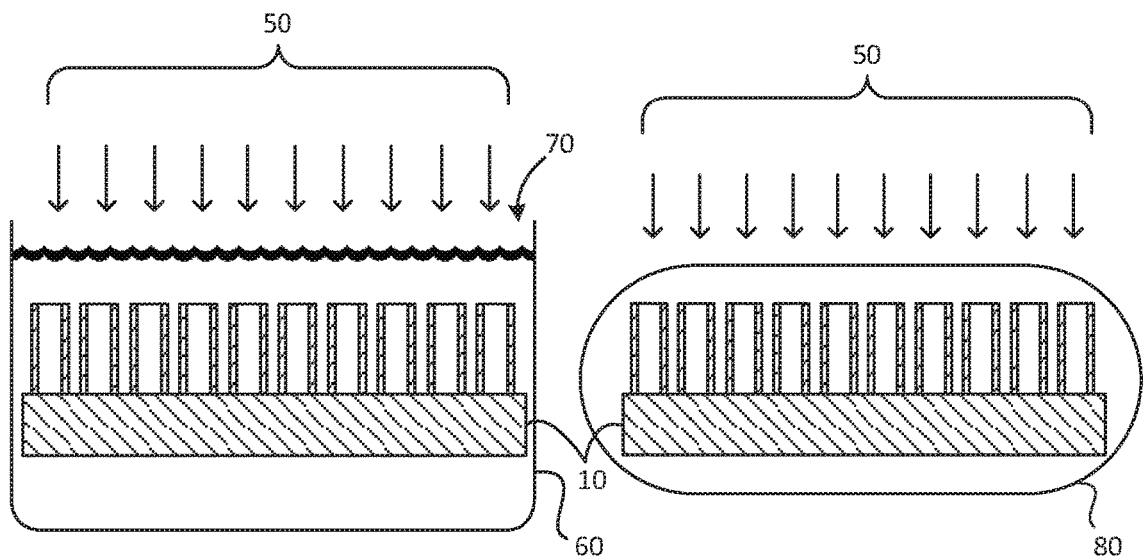

Referring now to FIGS. 2A-D, FIG. 2A illustrates the nanotube surface 20 of FIG. 1A with organic matter contaminants 35 present on the nanotube surface 20 of the medical device 10. FIGS. 2B-2D depict various ways of treating the nanotube surface 20 of FIG. 2A with UV radiation 50 to remove these organic matter contaminants 35 while the nanotube surface 20 is in various states including, but not limited to: a dry state, a wet state, and a protected state. Example UV radiation characteristics may include, for example, UV light wavelengths between about 260 nm to 350 nm with 10 to 100 watts of power and about 0.05 to 10 mW/cm$^2$ intensity.

FIG. 2B illustrates the use of UV radiation 50 to remove the organic matter contaminants 35 from the nanotubes while the medical device 10 is in a "dry state" by shining UV radiation 50 down into the inner bores 30 of the nanotubes to remove organic matter contaminants 35 from the inner nanotube surfaces 31 of the nanotubes, as well as remove organic matter contaminants 35 from the outer nanotube surfaces 32 of the nanotubes. A "dry state" may be defined as a state in which the medical device 10 is substantially free from liquids.

FIG. 2C illustrates the use of UV radiation 50 to remove the organic matter contaminants 35 from the nanotubes while the medical device 10 is in a "wet state" by shining UV radiation 50 down into the inner bores 30 of the nanotubes to remove organic matter contaminants 35 from the inner nanotube surfaces 31 of the nanotubes, as well as remove organic matter contaminants 35 from the outer nanotube surfaces 32 of the nanotubes.

A "wet state" may be defined as a state in which the medical device 10 is in contact with one or more liquids.

For example, the medical device 10 may be placed in a container 60 and submerged, or at least partially submerged, in a liquid 70, such as a suitable cleaning solution, aqueous solution, solvent, alcohol solution, or other suitable liquid 70, while at the same time undergoing exposure to UV radiation 50. The use of a suitable liquid 70 may speed up and/or otherwise facilitate the UV radiation 50 cleaning process.

FIG. 2D illustrates the use of UV radiation 50 to remove organic matter contaminants 35 from the nanotubes while the medical device 10 is in a "protected state" by shining UV radiation 50 down into the inner bores 30 of the nanotubes to remove organic matter contaminants 35 from the inner nanotube surfaces 31 of the nanotubes, as well as remove organic matter contaminants 35 from the outer nanotube surfaces 32 of the nanotubes.

A "protected state" may be defined as a state in which the medical device 10 is encapsulated, or at least partially encapsulated, within a protective barrier 80 which separates, or at least partially separates, the medical device 10 from its surrounding environment.

For example, a medical device may be placed within a suitable medical device package (not shown) which may substantially prevent, or at least slow down, the passage of ambient air and contaminants through the medical device packaging in order to protect the medical device from becoming contaminated by the outside environment. In some cases the interior of the medical device package may also be pre-filled with a sterile/inert gas (e.g., Ar, $N_2$, and the like) to help further protect a medical device 10 placed therein. In additional cases, the interior of the medical device package may also be placed under a vacuum to help protect a medical device 10 placed therein.

The protective barrier 80 may also be made of materials that readily allow the passage of UV radiation 50 through the protective barrier 80, while at the same time substantially preventing, or at least slowing down, the passage of ambient air and contaminants through the protective barrier 80. For example, the protective barrier 80 may be made from a UV-transparent plastic, glass, quartz, or other material which readily allows the passage of UV radiation 50 through the protective barrier 80, while substantially preventing, or at least slowing down, the passage of contaminants and/or other matter through the protective barrier 80.

Figure 3A:
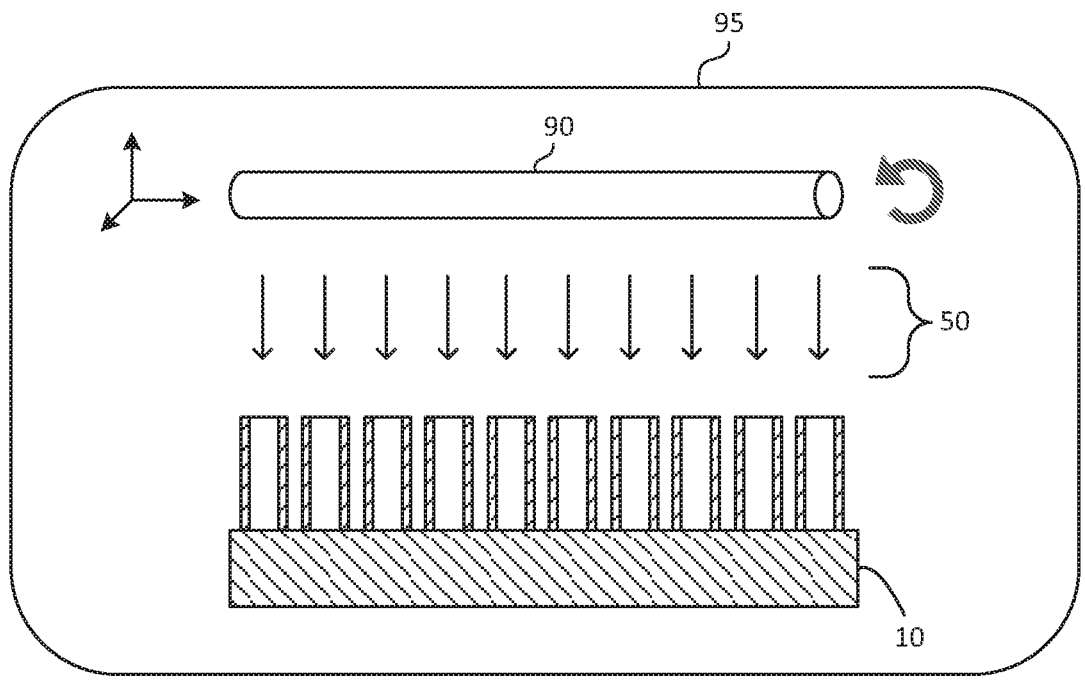
FIGS. 3A and 3B illustrate exemplary UV lamp configurations that are suitable for treating the nanotube surface of FIG. 1A.
Figure 3B:
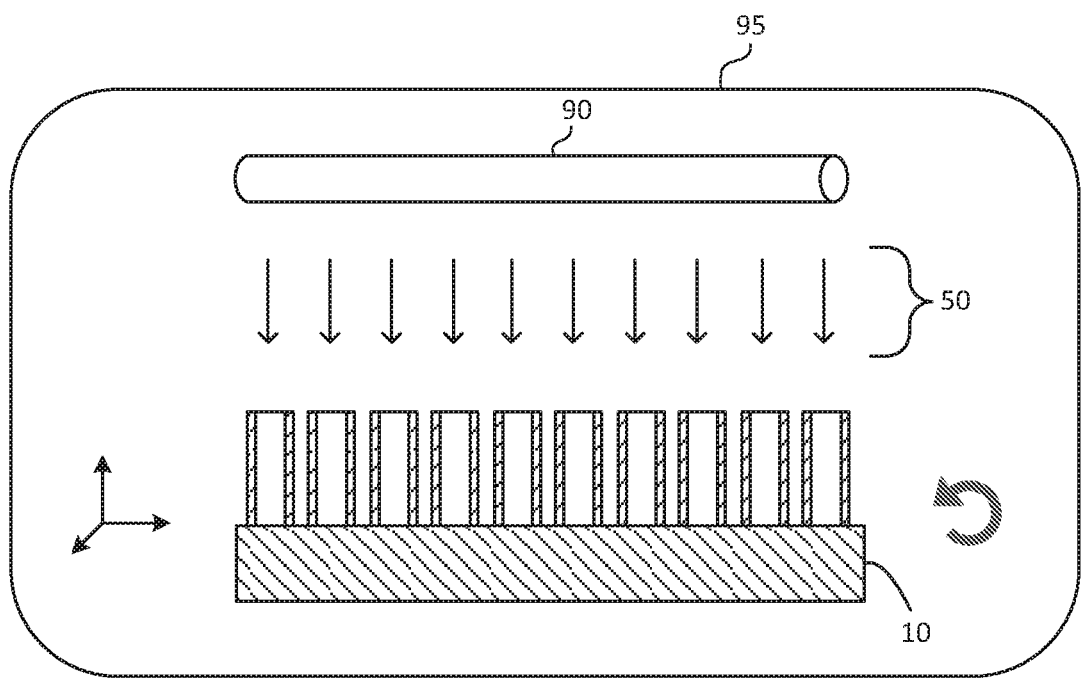

FIGS. 3A and 3B illustrate exemplary UV radiation configurations that may be used to treat the nanotube surfaces of medical devices disclosed herein. In particular, FIGS. 3A and 3B illustrate exemplary UV radiation configurations that may be used to enhance the UV radiation treatment of medical devices 10 that incorporate high-aspect-ratio TiO2 nanotube surfaces 20 with nanotubes which may be vertically aligned, have small-diameters (e.g., 30 to 300 nm diameters), and may be relatively tall (e.g., 100 nm-2,000 nm in height). These characteristics of high-aspect-ratio TiO2 nanotubes may make it difficult for UV radiation to illuminate all of, or at least a substantial portion of, the inner nanotube surfaces 31 and the outer nanotube surfaces 32 of the nanotubes to substantially remove any organic contaminants thereon.

FIG. 3A illustrates a medical device 10 enclosed within a chamber (or oven) 95 that is being exposed to UV radiation 50 emitted from at least one UV light source, such as a UV lamp 90. The UV lamp 90 may be rotated and/or translated relative to the medical device 10 in order to orient the UV lamp 90 in a plurality of different orientations relative to the nanotube surface 20. In this manner, the UV radiation 50 emitted from the UV lamp 90 may substantially illuminate all, or at least a substantial portion of, the inner nanotube surfaces 31 and the outer nanotube surfaces 32 to enhance removal of the contaminants. This process may be especially beneficial for medical devices 10 with complicated 3D geometries in order to provide UV exposure to all of the surfaces of the medical device 10. Moreover, the chamber (or oven) 95 may also be filled with any suitable gas, such as ambient air, $N_2$, Ar, and the like.

FIG. 3B illustrates the medical device 10 of FIG. 3A enclosed within the chamber (or oven) 95 and undergoing exposed to UV radiation 50 emitted from the UV lamp 90. However, in FIG. 3B, the medical device 10 may be rotated and/or translated relative to the UV lamp 90 in order to orient the nanotube surface 20 of the medical device 10 in a plurality of different orientations relative to the UV lamp 90. In this manner, the UV radiation 50 emitted from the UV lamp 90 may substantially illuminate all, or at least a substantial portion of, the inner nanotube surfaces 31 and the outer nanotube surfaces 32 to enhance removal of the contaminants.

In a further embodiment (not shown), both the UV lamp 90 and the medical device 10 may be rotated and/or translated relative to each other at the same time in order to orient the nanotube surface 20 of the medical device 10 in a plurality of different orientations relative to the UV lamp 90, such that the UV radiation 50 emitted from the UV lamp 90 may substantially illuminate all, or at least a substantial portion of, the inner nanotube surfaces 31 and the outer nanotube surfaces 32 and enhance removal of the contaminants.

It will be understood that the above embodiments describing rotational and/or translational movements of the medical device 10 and UV radiation 50 relative to each other may be combined with any other concept disclosed herein, such as performing these operations while the medical device 10 is in a dry, wet, and/or protected state and/or in combination with plasma treatments and/or heat treatments, as further described herein.

Figure 4:
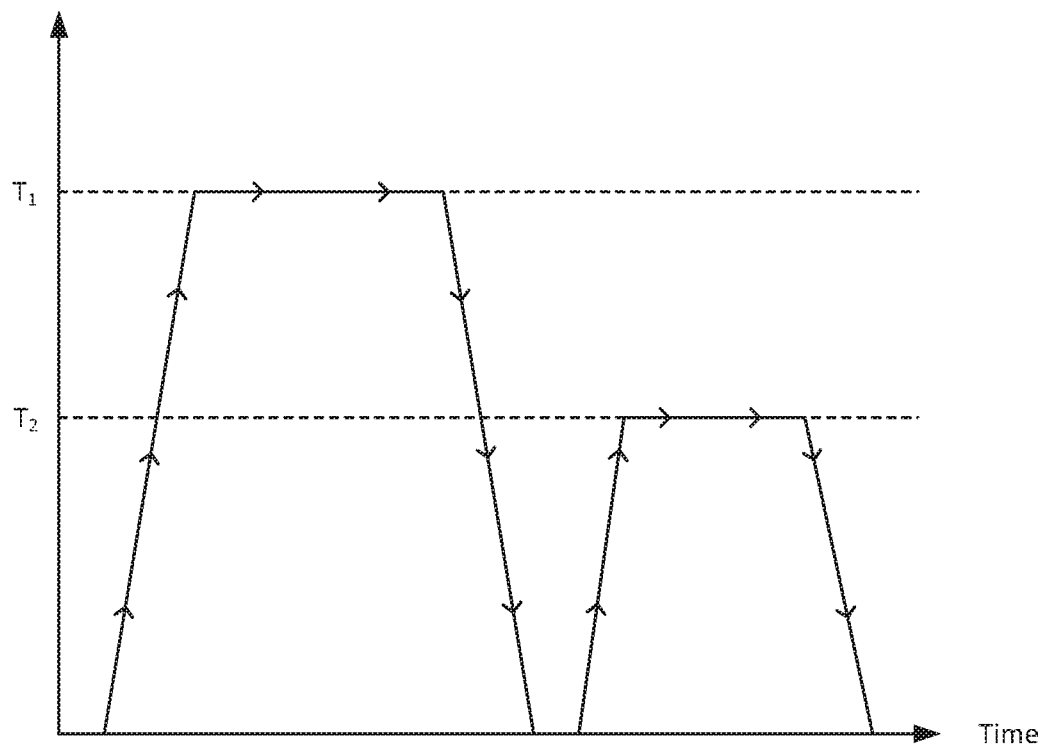
FIG. 4 illustrates a thermal-based method of treating a nanotube surface to re-activate an aged or contaminated nanotube surface.

FIG. 4 illustrates a thermal-based method of treating a nanotube surface 20 to re-activate an aged or contaminated nanotube surface 20. For example, heating-based removal of an organic film layer or other carbonaceous layer accumulated can be performed on the TiO2 nanotube surfaces 20 previously discussed herein.

TiO2 nanotube surfaces 20 may undergo an additional crystallization annealing process through exposure to a crystallization annealing temperature, after an anodization process has been performed, in order to form the more desirable anatase phase of TiO2. This crystallization annealing temperature may generally be performed at a temperature (Ti) of about 500° C. to 550° C., as shown in FIG. 4.

The heating temperature for removal of organic contaminants from the TiO2 nanotube surfaces 20 may advantageously be set at a lower temperature ($T_2$), such as about 400° C. or lower, so as to minimize thermal cycling induced by Coefficient of Thermal Expansion (CTE) mismatch between different materials and associated weakening of the interface between the Ti matrix and TiO2 nanotube layer. This nanotube re-activation heat treatment process may advantageously also be used with limited frequency so as to avoid fatigue-based micro-cracking and/or delamination of the TiO2 nanotube layer from the Ti (or Ti—Al—V based alloy, etc.).

Accordingly, in some embodiments a medical device 10 may be exposed to an elevated temperature that is below a crystallization anneal temperature of a nanotube surface associated with the medical device 10. In some embodiments, the maximum temperature may be limited to 400° C. or less. However, it will also be understood that any suitable temperature above 400° C. and/or below 400° C. may also be used, depending on the specific materials and/or construction of the medical device 10 undergoing heat-based treatment. Relatively slow heating and/or cooling rates may also be used during heat-based treatment in order to further minimize thermal stresses to the medical device 10. Moreover, heat-based treatment may also be combined with any other treatment or method disclosed herein.

Figure 5A:
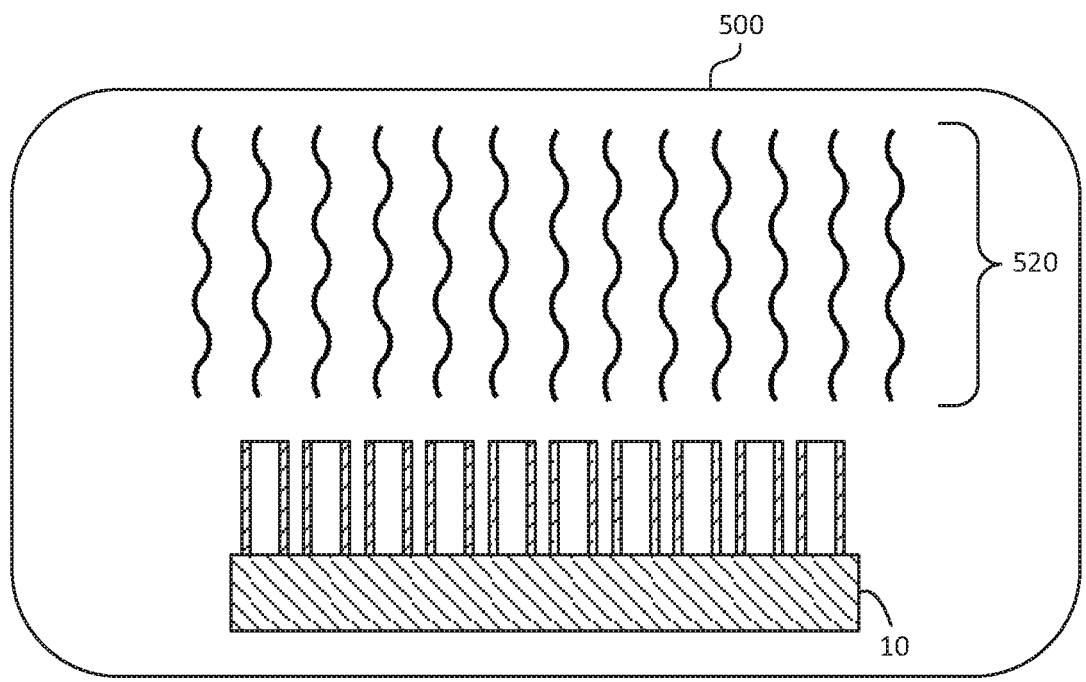
FIGS. 5A and 5B illustrate plasma-based methods of treating a nanotube surface to achieve rapid decomposition of organic contaminants from the nanotube surface of FIG. 1A.
Figure 5B:
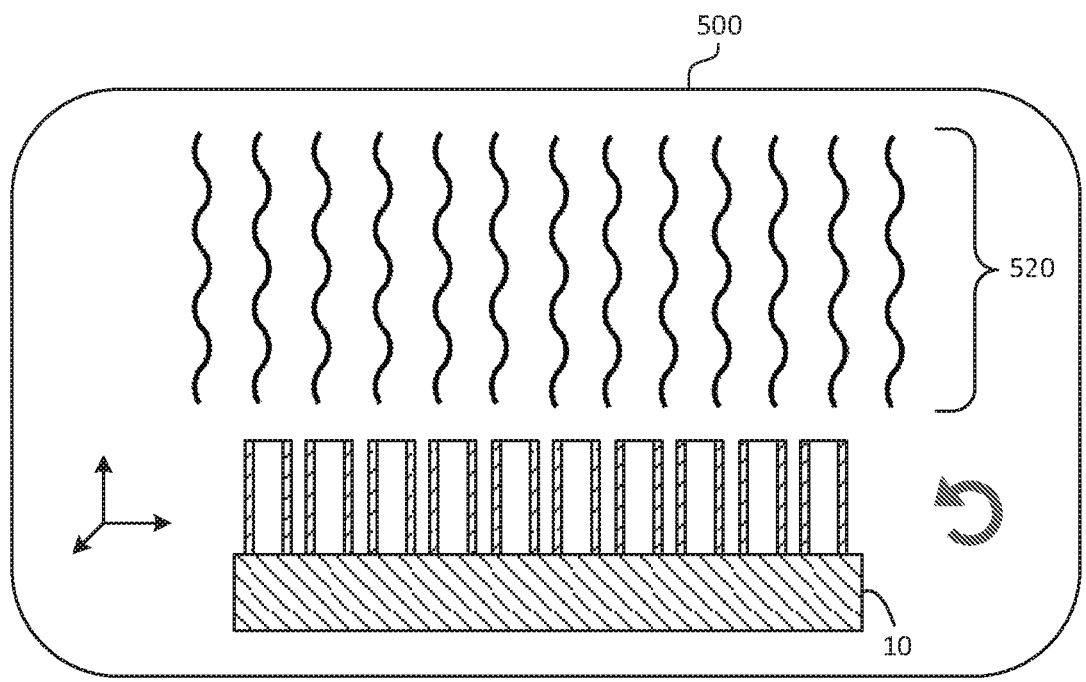

FIGS. 5A and 5B illustrate plasma-based methods of treating a nanotube surface of a medical device in order to achieve rapid decomposition of organic contaminants from the nanotube surface of the medical device.

FIG. 5A shows a medical device 10 that is placed within a plasma chamber 500 and exposed to a plasma 520. Plasma 520 may breakdown organic or carbon containing contaminants in a relatively short period of time (e.g., usually minutes rather than hours). This method may be desirable for achieving high-throughput re-activation of hydrophilic TiO2 nanotube surfaces. Suitable plasmas for this process may include, but are not limited to: oxygen-based plasma, argon-based plasma, nitrogen-based plasma, and the like.

FIG. 5B shows the medical device 10 of FIG. 5A enclosed within the plasma chamber 500 and undergoing exposure to the plasma 520. However, in FIG. 5B, the medical device 10 may also be rotated and/or translated within the plasma chamber 500 relative to the plasma 520 within the chamber 500 in order to orient the nanotube surface 20 of the medical device 10 in a plurality of different orientations relative to the plasma 520. In this manner, the plasma 520 may more quickly and/or more substantially infiltrate all, or at least a substantial portion of, the inner nanotube surfaces 31 and the outer nanotube surfaces 32 to enhance removal of the contaminants.

In a further embodiment (not shown), the plasma 520 within the chamber 500 may itself be rotated and/or translated within the plasma chamber 500 relative to the medical device 10 in order to further orient the nanotube surface 20 of the medical device 10 in a plurality of different orientations relative to the plasma 520. In this manner, the plasma 520 may more quickly and/or more substantially infiltrate all, or at least a substantial portion of, the inner nanotube surfaces 31 and the outer nanotube surfaces 32 to enhance removal of the contaminants by the plasma 520.

In an additional embodiment (not shown), both the plasma 520 and the medical device may be rotated and/or translated within the plasma chamber 500 relative to each other at the same time in order to orient the nanotube surface 20 of the medical device 10 in a plurality of different orientations relative to the plasma 520 and allow the plasma 520 to more quickly and/or more substantially infiltrate all, or at least a substantial portion of, the inner nanotube surfaces 31 and the outer nanotube surfaces 32 to enhance removal of the contaminants by the plasma 520.

It will also be understood that the above described plasma-based treatments may be combined with any other treatment(s) or method(s) disclosed herein.

In some embodiments (not shown), a medical device 10 may include surface nanotubes 20 made from oxides having at least one of: Ti, Zr, V, Ta, Nb, Hf, Mo, and/or W. The surface nanotubes 20 of the medical device 10 may exhibit an increase in its super-hydrophilic properties after exposure to at least one condition that at least partially removes contaminants from the surface nanotubes 20 of the medical device 10. The at least one condition may be selected from: ultraviolet light, an elevated temperature (e.g. 500° C. or less), and/or a plasma. Furthermore, the surface nanotubes 20 of the medical device 10 may substantially maintain their increased super-hydrophilic properties after undergoing a storage period of at least three months within a protected environment. The protected environment may include at least one of: a protective gas environment, a sealed environment, a vacuum-sealed environment, a plastic-wrapped environment, a metal-foil-wrapped environment, and the like.

Moreover, the super-hydrophilic properties of the surface nanotubes 20 may be further verified after the medical devices has completed the storage period of at least three months within the protected environment. For example, the super-hydrophilic properties of the surface nanotubes 20 may be verified by performing a water droplet contact angle test whereupon the surface nanotubes 20 may exhibit a water droplet contact angle of less than about 5 degrees, in one non-limiting example. In another non-limiting example, the surface nanotubes 20 may exhibit a water droplet contact angle of less than about 2 degrees. In still further non-limiting examples, the surface nanotubes 20 may exhibit a water droplet contact angle of about 5 to 20 degrees.

Figure 6:
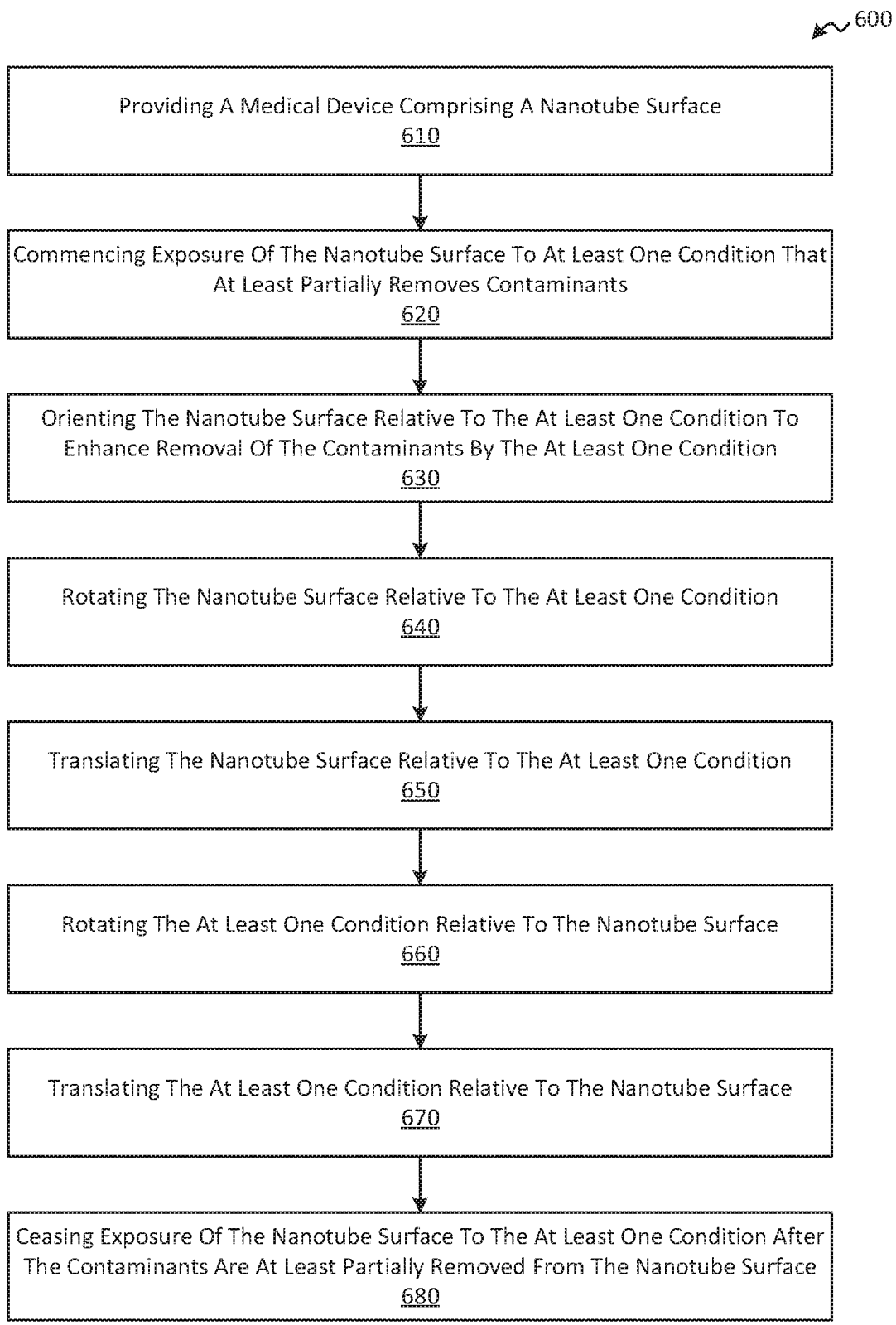
FIG. 6 illustrates a method of treating a nanotube surface to remove organic contaminants.

FIG. 6 illustrates a method 600 of treating a nanotube surface 20 in order to remove organic contaminants. The method 600 may include any of the treatments disclosed herein including: UV radiation exposure, heat-based treatments, plasma-based treatments, and/or any combinations thereof.

The method 600 may begin with a step 610 in which a medical device 10 comprising a nanotube surface 20 may be provided. Any type of medical device 10 disclosed herein may be provided and the medical device 10 that is provided may further include any type of nanotube surface 20 described herein.

Once a suitable medical device 10 with nanotube surface 20 has been provided, the method 600 may then proceed to a step 620 in which the nanotube surface 20 of the medical device 10 may be exposed to at least one condition that at least partially removes contaminants from the nanotube surface 20 of the medical device 10. As previously mentioned, the method 600 may include any of the treatments disclosed herein including: UV radiation exposure, heat-based treatments, plasma-based treatments, and combinations thereof.

In at least some embodiments, the method 600 may then proceed through one or more of the following steps (630, 640, 650, 660, and 670) of the method 600. However, it will be understood that these steps are not required.

For example, in at least one embodiment the method 600 may proceed to a step 630 in which the nanotube surface 20 may be oriented relative to the at least one condition to enhance removal of the contaminants by exposure to the at least one condition. This may be accomplished by additionally proceeding through one or more of steps 640, 650, 660, and 670 of the method 600.

For example, in at least one embodiment, the method 600 may proceed to a step 640 in which the nanotube surface 20 may be oriented relative to the at least one condition by rotating the nanotube surface 20 relative to the at least one condition. The at least one condition including: UV radiation, heat, plasma, and/or combinations thereof.

In at least one embodiment, the method 600 may alternatively, or in addition thereto, proceed to a step 650 in which the nanotube surface 20 may be oriented relative to the at least one condition by translating the nanotube surface 20 relative to the at least one condition.

Furthermore, in at least one embodiment the method 600 may alternatively, or in addition thereto, proceed to a step 660 in which the at least one condition may be oriented relative to nanotube surface 20 by rotating the at least one condition relative to the nanotube surface 20. Again, the at least one condition may include UV radiation exposure, heat-based treatments, plasma-based treatments, and/or combinations thereof.

Moreover, in at least one embodiment the method 600 may alternatively, or in addition thereto, proceed to a step 670 in which the at least one condition may be oriented relative to nanotube surface 20 by translating the at least one condition relative to the nanotube surface 20.

Once the nanotube surface 20 of the medical device 10 has been sufficiently cleaned of contaminants by any or all of the preceding steps, the method 600 may proceed to a step 680 in which exposure of the nanotube surface 20 of the medical device 10 to the at least one condition may be ceased after the contaminants have been at least partially removed from the nanotube surface 20, and the method 600 may end.

It will be understood that any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It is understood that the above-described embodiments are illustrative of only a few of the many possible specific embodiments which can represent applications of the present disclosure. Numerous and varied other arrangements can be made by those skilled in the art without departing from the spirit and scope of the disclosure. For example, the methods disclosed herein are applicable to non-implant devices such as drug delivery structures, stem cell differentiation substrates, cell-culture devices, biomaterials adhesion promoting structures, and so forth.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A method for removing organic contaminants from a medical device comprising a nanostructured surface having a water droplet contact angle, the method consisting of:
   commencing exposure of the nanostructured surface to a plasma selected to break down the organic contaminants, the nanostructured surface comprising a nanotube surface covering at least a portion of a surface of the substrate and having a water droplet contact angle, the nanotube surface comprising a plurality of nanotubes comprising:
      a plurality of inner nanotube surfaces;
      a plurality of outer nanotube surfaces; and
      an oxide nanotube coating formed over the plurality of inner nanotube surfaces and outer nanotube surfaces; and
   commencing exposure of the nanotube surface to ultraviolet light at 0.05 to 10 mW/cm$^2$ intensity, with a wavelength ranging from 260 nm to 350 nm at 10 to 100 Watts of power;
   optionally, commencing exposure of the nanotube surface to an elevated temperature of about 400° C.; and
   ceasing exposure of the nanostructured surface after the organic contaminants are removed from the nanotube surface, including the inner nanotube surfaces and the outer nanotube surfaces, to an extent sufficient to reduce the water droplet contact angle to 20° or less.

2. The method of claim 1 wherein the nanotubes comprise TiO2 nanotubes ranging from 30 to 300 nm in diameter and ranging from 100 to 2,000 nm height.

3. The method of claim 1 wherein the nanostructured surface further comprises at least one characteristic selected from:
   randomly structured nanopores;
   randomly structured nanorods;
   periodic structured nanopores; and
   periodic structured nanorods.

4. The method of claim 1, wherein commencing exposure of the nanotube surface to ultraviolet light consists of commencing exposure of the nanotube surface to the ultraviolet light while the nanostructured surface is in at least one state selected from:
   a dry state;
   a wet state; and
   a protected state.

5. The method of claim 1, consisting of commencing exposure of the nanotube surface to the elevated temperature below a crystallization anneal temperature of the nanostructured surface.

6. The method of claim 1 wherein the nanotubes are vertically aligned on the nanostructured surface with nanotube lateral dimensions less than 1,000 nm and nanotube heights less than 10 um.

7. The method of claim 1, wherein the plasma comprises at least one of: an Oxygen-based gas, an Argon-based gas, and a Nitrogen-based gas.

8. The method of claim 1, wherein the medical device comprises at least one of:
   an orthopedic implant;
   a dental implant;
   an in vitro biomedical implant;

an in vivo biomedical implant;
a cell growth device; and
a drug delivery device.

9. The method of claim 1, wherein the oxide nanotube coating comprises at least one of: Zr, V, Ta, Nb, Hf, Mo, W, or their oxides, by at least 50% weight.

10. The method of claim 1, wherein the oxide nanotube coating is formed from alloys containing at least one of Ti or TiO2 by at least 50% weight.

11. The method of claim 6 wherein at least part of the nanostructured surface further comprises at least one coating selected from:
a coating comprising hydroxyapatite, the coating comprising hydroxyapatite having a thickness of at least 2 nm;
a coating comprising calcium;
a coating comprising potassium;
a coating comprising Ta;
a coating comprising Ta-oxide;
a coating comprising at least one biological agent, wherein the coating comprising the at least one biological agent is at least partially present on the plurality of inner nanotube surfaces;
a coating comprising at least one catalyst, wherein the coating comprising the at least one catalyst is at least partially present on the plurality of inner nanotube surfaces;
a coating comprising at least one cell-growth-stimulating agent, wherein the coating comprising the at least one cell-growth-stimulating agent is at least partially present on the plurality of inner nanotube surfaces; and
a coating comprising at least one antibiotic, wherein the coating comprising the at least one antibiotic is at least partially present on the plurality of inner nanotube surfaces.

12. The method of claim 9, wherein the oxide nanotube coating is formed from an alloy containing V or V oxide.

13. The method of claim 10, wherein the oxide nanotube coating comprises TiO2 anatase crystals.

14. The method of claim 10, wherein the oxide nanotube coating has a thickness of at least 30 nm.

15. The method of claim 10, wherein the oxide nanotube coating covers at least 70% of a total surface of the medical device.

16. The method of claim 11, wherein the at least one coating comprises potassium.

17. A method for removing organic contaminants from a medical device, the medical device comprising:
a substrate; and
a nanotube surface covering at least a portion of a surface of the substrate and having a water droplet contact angle, the nanotube surface comprising:
a plurality of nanotubes comprising:
a plurality of inner nanotube surfaces;
a plurality of outer nanotube surfaces; and
an oxide nanotube coating formed over the plurality of inner nanotube surfaces and outer nanotube surfaces;
wherein the method consists of:
commencing exposure of the nanotube surface, including the inner nanotube surfaces and the outer nanotube surfaces, to a plasma selected to break down the organic contaminants, selected from the group consisting of Oxygen-based gases, Argon-based gases, and Nitrogen-based gases;
commencing exposure of the nanotube surface to ultraviolet light at 0.05 to 10 mW/cm$^2$ intensity, with a wavelength ranging from 260 nm to 350 nm at 10 to 100 Watts of power;
commencing exposure of the nanotube surface to an elevated temperature of about 400° C.; and
ceasing exposure of the nanotube surface to the plasma, ultraviolet light, and elevated temperature after the organic contaminants are removed from the nanotube surface, including the inner nanotube surfaces and the outer nanotube surfaces, to an extent sufficient to reduce the water droplet contact angle to 20° or less.

18. The method of claim 17, wherein the oxide nanotube coating covers at least 70% of a total surface of the medical device.

19. The method of claim 17, wherein the oxide nanotube coating is formed from alloys containing at least one of Ti or TiO2 by at least 50% weight.

20. The method of claim 19, wherein the oxide nanotube coating comprises TiO2 anatase crystals.

21. The method of claim 19, wherein the oxide nanotube coating has a thickness of at least 30 nm.

* * * * *